United States Patent [19]

Caldwell et al.

[11] Patent Number: 5,112,736
[45] Date of Patent: May 12, 1992

[54] DNA SEQUENCING USING FLUORESCENCE BACKGROUND ELECTROBLOTTING MEMBRANE

[75] Inventors: Karin D. Caldwell; Tun-Jen Chu, both of Salt Lake City; William G. Pitt, Orem, all of Utah

[73] Assignees: University of Utah, Salt Lake City; Brigham Young University, Provo, both of Utah

[21] Appl. No.: 365,693

[22] Filed: Jun. 14, 1989

[51] Int. Cl.⁵ .............................................. C12Q 1/68
[52] U.S. Cl. ................................... 435/6; 435/91; 435/129; 435/291; 435/313; 435/805; 436/501; 436/113; 436/172; 436/800; 436/807; 536/27; 935/17; 935/19; 935/77; 935/86; 935/88
[58] Field of Search ................. 435/6, 91, 129, 291, 435/313, 805; 436/501, 113, 172, 800, 807; 536/27; 935/17, 19, 77, 86, 88

[56] References Cited

U.S. PATENT DOCUMENTS

| | | | |
|---|---|---|---|
| 3,847,652 | 11/1974 | Fletcher et al. | 117/93.1 |
| 4,299,916 | 11/1981 | Litman et al. | 435/6 |
| 4,560,458 | 12/1985 | Ueno et al. | 204/165 |
| 4,775,619 | 10/1988 | Urdea | 435/6 |
| 4,942,124 | 7/1990 | Church | 435/6 |

OTHER PUBLICATIONS

Sipehia et al. (1986) Biomaterials, vol. 7, pp. 471-473.
Wydeven et al., (1974) in "Techniques and Applications of Plasma Chemistry", (EDs. Hollahan et al., John Wiley & Sons) pp. 215-228.

*Primary Examiner*—Amelia Burgess Yarbrough
*Assistant Examiner*—Ardin H. Marsche

[57] ABSTRACT

A method for the multiplex sequencing on DNA is disclosed which comprises the electroblotting or specific base terminated DNA fragments, which have been resolved by gel electrophoresis, onto the surface of a neutral non-aromatic polymeric microporous membrane exhibiting low background fluorescence which has been surface modified to contain amino groups. Polypropylene membranes are preferably and the introduction of amino groups is accomplished by subjecting the membrane to radio or microwave frequency plasma discharge in the presence of an aminating agent, preferably ammonia. The membrane, containing physically adsorbed DNA fragments on its surface after the electroblotting, is then treated with crosslinking means such as UV radiation or a glutaraldehyde spray to chemically bind the DNA fragments to the membrane through said smino groups contained on the surface thereof. The DNA fragments chemically bound to the membrane are subjected to hybridization probing with a tagged probe specific to the sequence of the DNA fragments. The tagging may be by either fluorophores or radioisotopes. The tagged probes hybridized to said target DNA fragments are detected and read by laser induced fluorescence detection or autoradiograms. The use of aminated low fluorescent background membranes allows the use of fluorescent detection and reading even when the available amount of DNA to be sequenced is small. The DNA bound to the membrances may be reprobed numerous times.

26 Claims, No Drawings

DNA SEQUENCING USING FLUORESCENCE BACKGROUND ELECTROBLOTTING MEMBRANE

This Invention was made with Government support under Contract No. DE-FG02-88ER60700 awarded by the Department of Energy. The Government has certain rights in this invention.

FIELD OF THE INVENTION

This invention relates to sequencing of DNA and similar negatively charged moieties using an electroblotting membrane having low fluorescence background which has been surface modified to contain amino groups. More particularly, this invention relates to the binding of nucleic acid fragments, electrotransferred from a sequencing gel, onto the surface of a low fluorescence membrane which has been surface modified to contain amino groups to assist in the binding of the nucleic acid to the membrane and to the hybridization probing and sequence identification of the nucleic acid fragments.

BACKGROUND OF THE INVENTION

The DNA sequencing methods which have emerged since about 1970 have played a key role in the development of modern molecular biology and have enabled the investigation of such important problems as the molecular mechanism of life, the regulation and activity of genes, the localization of genes responsible for inherent characters and diseases, the structure of chromosomes, the disease-causing factors of bacteria and viruses, (e.g. HIV for AIDS), etc. Through sequencing techniques many useful and practical applications have developed, i.e. genetic diseases can be diagnosed, certain sequence locations are now used by law enforcement agencies as 'finger prints' of individuals, genetic research in agriculture is speeded up using specific DNA sequences.

One technique for DNA sequencing referred to as the Gilbert method, [Gilbert et al., Proc. Natl. Acad. Sci., 74, 560, (1977), and Gilbert, Science, 214, 1305 (1981)] and is based on a chemical cleavage process which breaks a 5' end $^{32}$P-labeled DNA at specific bases. Using purine-specific dimethylsulphate and pyrimidine-specific hydrazine, four chemical reactions yield DNA fractions according to their end base grouping. The products are then resolved by size, using polyacrylamide gel electrophoresis and the pattern of bands are read via autoradiography.

The Sanger method [Sanger et al, Proc. Natl. Acad. Sci., 74, 5464, (1977)] sequences single stranded DNA by an enzymatic chain-terminating method. A preliminary $^{32}$P-labeled primer is incubated with the DNA template to be analyzed in the presence of DNA polymerase and a proper mixture of 'regular' deoxy- and 'chain terminatory' dideoxy-ribonucleoside triphosphates. The template is copied by the appropriate nucleotides (A, G, C or T) into the complementary strand which grows from the 3' end of the template until a chain terminator is built in. If the terminator is a ddTTP, all copies of the template will end in a T (thymine base). The procedure is repeated with A (adenine), G (guanine) and C (cytosine) terminators respectively. These segments for each procedure (A, G, C or T) are resolved by gel electrophoresis and read via autoradiography.

The Sanger chain terminating method is currently the most popular DNA sequencing procedure since it is easy to read and easy to automate However, both the Sanger and Gilbert methods have serious drawbacks. The manual procedures are repetitive, laborious and time consuming. The DNA sequencing of some gene region in preparation for an actual research problem often takes several years. When one considers that an individual gene often consists of several hundred thousand base pairs, that a chromosome often consists of thousands of genes and a human genome consists of 46 chromosomes, the numbers of steps in sequencing of a human genome becomes astronomical. It is stated that the number of base pairs in a human genome is over three billion. Molecular biologists also have strong interests in mapping the sequence of genes from other species in both plant and animal life including, but not limited to, mice, yeasts, bacteria and viruses.

In addition to slow manual procedures, there is also the problem of using radioisotopes for labeling. They are hazardous to health, expensive, unstable for storage and difficult to dispose of in an environmentally sound way.

It has been proposed that the limitations of using radioisotopes might be overcome by use of fluorescent dye labeling followed by gel electrophoresis. Various methods have been proposed using fluorophores such as fluorescein iodoacetamide, succinyl fluorescein derivatives. It has also been proposed to use four different colored fluorophores each being specific of each of the four bases contained in DNA. As attractive at these concepts may be they also have inherent drawbacks in that only a single set of sequence data can be obtained from each gel electrophoresis. Gel electrophoresis is one of the most laborious and time-consuming steps.

Southern [J. Molecular Biol., 98, 503 (1975)] developed a technique for blotting DNA from a gel onto a cellulose nitrate membrane in much the same manner as using an ink blotter. An improvement of this technique was made by Church and Gilbert [Proc. Natl. Acad. Sci., 81, 1991 (1988)] who applied an electric field to transfer unlabeled DNA fragments onto a nylon membrane followed by a subsequent ultraviolet-crosslinking step to bind the DNA covalently to the nylon. A hybridization step with short $^{32}$P-labeled single strand oligonucleotide produced the image of the DNA sequence ladder. This method is a significant advance over other methods in that numerous different sequences can be mixed, loaded and separated on a single sequencing gel, followed by a transfer to a nylon membrane and probed many times using different complementary probes and producing separate autoradiographs for each sequence in the cycle. This method, referred to as 'multiplexing' [Church et al., Science, 240, 185 (1988)] still requires the expense and time consuming work of producing and handling a large number of autoradiographs. Nylon membranes are not suited for use with DNA segments tagged with fluorophores because polyamides exhibit an unacceptably high background fluorescence.

A method of sequencing DNA using fluorophores may be found, for example, in Middendorf, U.S. Pat. No. 4,729,947 where segmented DNA strands are marked at one end with biotin. Using a continuous method of electrophoresis, they are moved into avidin marked with fluorescein. Avidin has a high affinity for biotin. The shorter strands, being resolved first, combine with the avidin and are scanned and the signals decoded and the process continues as the longer strands are resolved. There is no use of blotting membranes or materials.

Another method is found in Van den Engh et al, U.S. Pat. No. 4,770,992 wherein chromatin (comprising DNA and protein) is first contacted with a cross-linking agent for the protein to provide a substantially rigid chromatin particle. The DNA is then separated into individual DNA strands and contacted with a complementary polynucleotide probe specific for the DNA sequence of interest. The probe is marked with a fluorescent label. The fluorophore tagged DNA sequences are then detected by subjecting the probe to a suitable light source using flow cytometry and detecting the light emitted by the fluorescent label so as to identify the preselected DNA sequence. However, this method does not provide a means for stripping the probe and reprobing the sample using different DNA sequences as can be accomplished on an appropriately designed membrane.

SUMMARY OF THE INVENTION

It is an object of the present invention to provide a method for sequencing DNA using multiplex reprobing procedures based on a system using electroblotting membranes allowing either a direct spectroscopic readout of separated DNA fragments tagged with fluorophores instead of using delayed autoradiography or, in the alternative, using radioisotopes and reading the results by autoradiography.

It is a further object of this invention to provide an electroblotting membrane for DNA sequencing exhibiting low background fluorescence and having a modified surface containing amino groups providing a high binding capacity for DNA fragments and similarly charged molecules.

These and other objects may be accomplished by using, as an electroblotting membrane, a neutral non-aromatic polymer which has been surface modified to contain amino groups. The amino groups are attached to the surface of the polymer membrane, such as polypropylene, by subjecting the membrane to ammonia in the presence of radio frequency plasma discharge (RFPD). The membrane has good physical stability, low electro-resistance to electroblotting procedures and exhibits a low fluorescence background.

In the analysis of a DNA sample using multiplexing sequencing, a target DNA mixture is first sequenced using the Sanger chain-terminating method. The mixture of copied DNA sequences, which are thus generated, are then separated according to molecular weight by standard gel electrophoresis and electrotransferred to the amino group containing electroblotting membrane.

The amino groups on the membrane are positively charged and adsorb the polyanionic DNA fragments electrotransferred from the sequencing gel to the membrane. The membrane is then treated with either UV irradiation or, preferably, a crosslinking agent such as glutaraldehyde, to covalently bond the DNA to the amino groups of the membrane. When using glutaraldehyde as the crosslinking agent, any excess aldehyde groups are passivated by treating the membrane with an agent such as ethanolamine. The membrane, as thus treated, contains DNA sequences covalently bound to the membrane which provides a permanent record of the separation.

Preferably a fluorophore labeled probe specific to the sequence is then hybridized with the target DNA and the 'sequence ladders' are identified by laser induced fluorescence or other appropriate means for detecting fluorescent labeled DNA. The data obtained can be transferred directly to a computer from the detector without the lengthy exposure to an x-ray film and manual key-in required when using radioactive probes. After identification, the probe can be washed off and the next probe can be introduced to repeat the cycle. Depending upon the stability of the DNA linked to the membrane, reprobing can be repeated up to a hundred, or perhaps even hundreds of times.

Although less desirable, after the electroblotting procedure the probing may be done using radioisotope tagged DNA instead of fluorophores and the results can be determined using standard autoradiography.

DETAILED DESCRIPTION OF THE INVENTION

The sequencing methods which follow are best understood by a separate description of the various components utilized in the integrated overall process.

Preparation of Aminated Electroblotting Membranes

The presently commercially available nylon, or polyamide, membranes used for DNA sequencing using autoradiography possess a high fluorescence background which is unsuitable for use with a fluorescence based detection system. To enable detection of nucleotides down to the necessary femtomole ($10^{-15}$) level, the membrane must have a low fluorescence background, high DNA retention and high specific binding capabilities. In addition, it must show good mechanical properties as well as shape stability.

As previously stated, the membrane used for electroblotting is a neutral non-aromatic polymer which has been surface modified to contain amino groups. Representative polymers include suitable hydrocarbons, fluorocarbons, chlorofluorocarbons, vinyl alcohols and vinyl chlorides and copolymers and blends thereof. Exemplary of such polymers are polypropylene (PP), polyethylene (PE), polytetrafluoroethylene (PTFE), polyvinylidenefluoride (PVDF), polyvinylchloride (PVC), polyfluoroethylene-propylene (PFEP), ethylenevinylalcohol (EVAL), and polyethylenechlorotrifluoroethylene (PECTFE) and blends and copolymers thereof. Of the polymers listed above, those which a exhibit low fluorescence background generally have simple saturated backbones, such as fluorocarbons and hydrocarbons. Exemplary of such are polypropylene (PP), polyethylene (PE) and polytetrafluoroethylene (PTFE) and these will be specifically referred to herein with polypropylene (PP) being particularly preferred and illustrated. However, all polymer membranes which exhibit sufficient low fluorescence and which may be suitably surface modified with amino groups are not to be excluded.

Membranes suitable for derivatization with amino groups are those classified for microfiltration and are generally commercially available. For example, unmodified polypropylene membranes are marketed under such tradenames as Metricel (Gelman Sciences) and Celgard (Celanese). Because unmodified membranes are available commercially, only a brief description of their preparative methods will be given.

Polyolefin membranes may be prepared using a thermal phase-inversion process. In the thermal phase-inversion process a polymer is dissolved in a latent solvent at elevated temperatures. Upon cooling, the solvent becomes a non-solvent and a polymer phase, having a continuous porous network, separates or precipitates out. The residual non-solvent contained in the porous polymer network is removed by drying or similar methods. Polypropylene membranes, commercially available under the Metricel tradename, are made by this process and generally have a thickness of about 1 to 200 μm, and a pore size of between about 200 and 10,000 angstroms. Thinner membranes may desirably have a backing, such as polyethylene, to improve their physical properties.

Microporous membranes of the polyolefin and fluorocarbon variety may be prepared by stretching a homogeneous polymeric film of partial crystallinity. The polymer molecules of an extruded film align themselves in the machine direction and nucleate the formation of folded-chain lamellar microcrystallinities. The regions containing parallel lamellae are separated from one another by amorphous regions. In a stretching perpendicular to the lamella direction, at a temperature above the annealing temperature but below the melting temperature, the amorphous regions deform into fibrillar bridging which results in microporous structure in between. Polypropylene membranes, commercially available under the Celgard tradename, are made by this process and generally have a thickness of 1 to 200 um and a pore size of between about 200 and 10,000 angstroms. Again, thinner membranes may desirably be backed. PTFE membranes are also manufactured by a similar but different stretching process to induce porosity. In addition to uniaxial stretching, biaxial stretching is also employed. Therefore, the fibril directions in PTFE membranes are not always parallel to each other. These membranes are chemically very inert and hydrophobic so that they can function in very corrosive environments.

In order to be functional and achieve sufficient affinity of nucleotides, these polymers are necessarily surface modified by the introduction of amino groups. A feasible method for introducing amino groups onto the surface of these membranes is by use of plasma discharge in an ammonia or organic amine containing gas.

A plasma is an ionized gas which gains sufficient ionization energy from an electromagnetic field. It exhibits long range electromagnetic forces and becomes a conductor of electricity. Plasma consists of a mixture of electrons, atoms, positive and negative ions and neutral free radicals and is, over all, electrically neutral. Plasma energy sources include direct current, alternating current, radio frequency, microwaves, shock waves and lasers. The membranes used in this invention are particularly adaptable to surface modification using radio frequency plasma discharge (RFPD) and microwave frequency plasma discharge (MFPD). A cold plasma treatment, of the RFPD or MFPD type, affects only the surface layer of a solid material to a depth of about 100–1,000 angstroms leaving the remainder unmodified. The dry gas-solid interactions provides chemical flexibility and is usually free of undesired side reactions that often occur during solution reactions.

During direct current plasma discharge, the surface of electrically insulating materials, such as polymers, will charge up to the equilibrium value where current no longer flows. Low frequency alternating current plasma discharge is ineffective because of the time required to charge up. Most of the time the discharge is off. In RFPD and MFPD, the charge accumulated during a half cycle can be neutralized during the next half cycle.

Plasma technology is a powerful surface modification method. However, the plasma excitation process is inherently complicated. In RFPD and MFPD, electrons oscillate in response to the high frequency field, picking up enough energy for ionization. When the electrons impact with gas molecules a wide variety of reactions, such as ionization, dissociation, charge transfer and radical combinations occur in the gaseous phase, creating a variety of particles. The interactions between plasma particles and solid surfaces are usually classified into four types (1) abstraction of species from the surface, (2) rearrangement of bonds, (3) addition of entities singly to the surface and (4) polymerization of entities on the surface. Multiple reactions might occur at the same time; however, it is the addition of the amino groups that is desired to facilitate the attachment of nucleotide fragments to the polymeric membrane surface.

The polyolefin and fluorocarbon membranes utilized in the present invention are surface modified, via RFPD or MFPD discharge in ammonia gas or other suitable amine introducing entities such as $C_1-C_{10}$ aliphatic or cyclic amines. Such amines may be primary, secondary or tertiary. The hydrocarbon chain may be straight or branched, saturated or unsaturated. One or more amino groups may be attached to the hydrocarbon chain. Methyl amine, allyl amine, ethylenediamine, diaminocyclohexane and the like are exemplary. However, ammonia is the preferred species. Many different species, ions or radicals, coexist in the plasma and multiple reactions with the polymer might occur. The most probable mechanism for attachment of amino groups to a polypropylene polymer is as follows:

$$\dot{N}H_2 + -CH_2-\dot{C}-CH_2- \longrightarrow$$
$$\phantom{\dot{N}H_2 + -CH_2-}CH_3$$

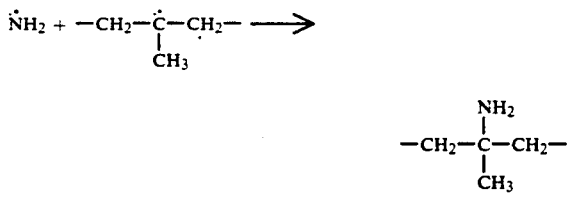

Polypropylene is more readily modifiable than polyethylene or PTFE because of the pendent methyl groups linked to a tertiary carbon backbone chain. The removal of hydrogens linked to such tertiary carbons is known to be the most favorable mechanism in radical formation during the plasma interaction. However, polyethylene and PTFE may also be similarly surface modified.

The degree of surface modification using RFPD or MFPD appears to be a function of plasma power and exposure time up to a point of equilibrium between abstraction and addition. The higher the power, the more free amine radicals are generated and the longer the exposure time, the more of these amine radicals collide with the surface and become attached as amino groups. Flow rates and pressures seem to have no major effect on the degree of derivatization.

The following procedures are illustrative of the surface modification of two types of polypropylene membranes.

Metricel membranes (Gelman Sciences) having pore sizes of 0.2 um and 0.1 um is one type and Celgard membranes (Celanese) having pore sizes of 0.04 um and 0.02 um are the second type.

RFPD Membrane Plasma Discharge Treatment

The membranes to be modified were mounted in an aluminum holder with glass legs which rested on one electrode. The membranes were positioned to be equidistant at 6 cm. from each electrode. The operational parameters, including gas flow rates, throttle pressure, process time, purge time, vent times, RF power and base pressure, were controlled by a microprocessor with a preset program.

The introduction of amines onto the surface of the membranes was carried out in a model PS0500 RFPD reactor from Plasma Science Inc. The reactor chamber had aluminum walls and provided an effective volume of 50 cm. high × 33 cm. wide × 40 cm. deep. The shelf electrodes were designed to expose samples to an even flow of gas everywhere on the shelf, giving a nearly uniform plasma distribution in the reaction region. The RF generator and impedance matching network provided 13.56 MHz RF excitation at about 5 KV voltage. Gas flow controllers allowed the inlet of up to three gases during an operation. A Roots vacuum pumping system provided two stage pumping down to millitorr pressure.

The process was carried out in three steps. The first consisted of an ammonia gas (refrigerant grade, 99.5%) discharge with operational parameters in the range of gas flow rate (100-500 μmole/sec), throttle pressure (0.1-0.5 torr), RF power (0-360 watts), and process time (0-3 min.) The second step was with the RF power turned off to let the membranes equilibrate in an ammonia atmosphere. In the third step, any surviving radicals were partially quenched with hydrogen gas (99.95%). Following the discharge and quenching steps, the modified membranes were sealed in plastic bags pending analysis. The parameters of each process step are shown in Table 1.

TABLE 1

| | Step No. | | |
|---|---|---|---|
| | 1 | 2 | 3 |
| | Step Type | | |
| | $NH_3$ Discharge | $NH_3$ Quench | $H_2$ Quench |
| $NH_3$ (μmole/sec) | 300 | 408 | — |
| $H_2$ (umole/sec) | — | — | 510 |
| Throttle (torr) | 0.375 | 2.0 | 1.0 |
| Process Time (min.) | 2.0 | 2.0 | 2.0 |
| Purge Time (min.) | — | — | — |
| Slow Vent (min.) | — | — | 2.0 |
| Vent (min.) | — | — | 1.0 |
| Pause Time (min.) | — | — | — |
| RF Power (watts) | 177 | — | — |
| Base Pressure (torr) | 0.020 | 0.300 | 0.050 |

XPS Analysis of Membranes

The membranes treated by RFPD were taken from the plastic bags and subjected to surface elemental analysis by X-ray Photoelectron Spectroscopy (XPS) using a model HP 5950 spectrometer controlled by a HP 5191 computer (both from Hewlett Packard). XPS is also referred to as ESCA (Electron Spectroscopy for Chemical Analysis). This technique provides an elemental analysis as well as information of chemical binding in a sampling depth of 20 to 200 angstroms depending on the sample and the take-off angle. In this analysis the take off angle was 17°.

The samples taken directly from the sealed plastic bags were analyzed with wide scans between 0 and 1000 eV. The C-1s, N-1s, and O-1s peaks were subsequently analyzed in narrow scans with 20 eV windows. The operation power was maintained at 400 watts and the flood gun was operated at 6 eV to compensate for the photoelectrons ejected from the sample surface. The pressure in the analysis chamber was $1 \times 10^{-9}$ torr. The degree of amino group introduction is determined as a function of the atomic percentage of nitrogen as analyzed by XPS.

Tables 2 and 3 which follow show the approximate percentage of atomic nitrogen as function of exposure time (Table 2) and RF power (Table 3). Other than varying the time and power the other parameters remained the same as in Table 1.

TABLE 2

| | N % on Surface of Modified Polymer | | | |
|---|---|---|---|---|
| Time (min) | Metricel 0.2 μm | Metricel 0.1 μm | Celgard 0.04 μm | Celgard 0.02 μm |
| 0.0 | 0.0 | 0.0 | 0.0 | 0.0 |
| 0.5 | 2.1 | 2.1 | 2.7 | 2.8 |
| 1.0 | 3.0 | 3.0 | 3.7 | 4.8 |
| 2.0 | 4.4 | 4.4 | 5.3 | 6.2 |
| 2.5 | 4.8 | 4.5 | 6.0 | 6.1 |
| 3.0 | 4.7 | 4.3 | 4.7 | 5.8 |

TABLE 3

| | N % on Surface of Modified Polymer | | | |
|---|---|---|---|---|
| Power (watt) | Metricel 0.2 μm | Metricel 0.1 μm | Celgard 0.04 μm | Celgard 0.02 μm |
| 0 | 0.0 | 0.0 | 0.0 | 0.0 |
| 60 | 2.2 | 1.6 | 2.2 | 2.2 |
| 120 | 4.0 | 4.0 | 4.4 | 6.2 |
| 177 | 4.2 | 4.5 | 4.6 | 6.4 |
| 230 | 4.5 | 4.3 | 4.5 | 6.2 |
| 300 | 4.7 | 4.3 | 3.9 | 6.0 |

As can be seen from the above tables, the resulting nitrogen atomic percentages increase as a function of increasing time and power until a maximum is reached which might reflect a saturation in which the addition and abstraction reactions are in equilibrium. From Table 2 it is seen that nitrogen atomic percentages are optimal at a discharge time of between about 2 and 3 minutes at an RF power of 177 watts and from Table 3 the nitrogen atomic percentages are maximum at an RF power of 177 watts at a constant discharge time of 2 minutes. Results were also determined as a function of varying ammonia flow rates and pressures but amino group introduction onto the membrane seemed unaffected by these parameters. However, this is not surprising since the fraction of ammonia molecules ionized is a very small amount, i.e. less than 1% in the free radical state and less than 0.1% in the ion state, of the gas in the reaction chamber. However, when using $C_1-C_{10}$ amines, the deposition of amino groups is more dependent upon flow rates and pressures.

SEM Analysis of Membranes

The membrane structure of the derivatized Metricel and Celgard polypropylene membranes were further analyzed by Scanning Electron Microscopy (JOEL-35SEM) with an applied voltage of 15 KV. Samples were prepared by silver coating and imaged with 6,000 to 10,000 times enlargement. The microstructures of the pores of the Celgard membranes were seen to be changed significantly during the plasma discharge process while those of the Metrical membranes were not. The Metricel membranes were more thermally stable than the Celgard. Some plasma induced deformation of the Celgard membranes was observed by the naked eyes while no such deformation was seen for the Metricel membranes. It is believed these differences are due to the manufacturing methods. Celgard membranes are made by consecutive steps of cold stretching, hot stretching and heat setting of extruded polypropylene films. They are heat sealable. During the plasma particle bombardment, the inelastic collision energy loss, or the heat of reaction, is dissipated to the membrane substrate, which relaxes from the unstable stretched state toward its original non-porous state. On the other hand, Metricel membranes are made by a hot solvent dissolution followed by a thermal quenching. The solution separates into two continuous phases and the pores appear when the solvent is extracted. Since the membranes were not stretched during manufacturing, residual stresses are absent and no relaxation is observed.

Mechanical Membrane Properties

In multiplex DNA sequencing, the membrane-linked DNA is to be repeatedly hybridized, washed, and detected. The surface modified membrane therefore, needs to be as tough and strong as possible to withstand the repetitive handling. A tension test was employed to characterize the mechanical properties of Metricel and Celgard membranes both before and after surface modification with amino groups. The membranes were each cut into strips 2.55 cm. wide and 10 cm. long. The thicknesses were measure by a micrometer and the cross-sectional areas calculated as listed in Table 4. After wetting, as would be done in an electroblotting procedure, each membrane was loaded on an stress-strain machine (Instron Model 1130) with a maximum load of 10 lbf. A constant extension rate of 5.08 cm/min was applied, and the load was recorded on a chart recorder running at a constant rate of 6 cm/min. Load and strain at break were determined and stress and elastic modulii were calculated. These mechanical properties are given in Table 4.

direction, this anisotropic membrane exhibits high tensile strength and can bear very high loading without breakdown.

However, as can be seen from Table 4, both Metrical and Celgard polypropylene membranes are changed during the RFPD treatment. Every RFPD treated polypropylene membrane is less extensible and more brittle than it is in unmodified form. This phenomenon is likely caused by the bombardment of plasma particles which break, not only the C—H bond, but also the polymer backbone. Shape stability and mechanical properties of these derivatized membranes for use in DNA sequencing can be improved by various means such as lamination of a suitable backing material such as polyethylene to the membrane or increasing the membrane thickness. Brittleness problems can be minimized by careful handling and automation of the electroblotting of the DNA on the membrane and if the hybridization and washing cycles will reduce the handling steps.

From the above description one skilled in the art can also adapt other suitable membranes having low background fluorescence properties to also contain amino groups on the surface thereof.

Background Fluorescence of Derivatized Membranes

Fluorescence is generated when a molecule relaxes from an excited state to a lower energy state. The excited states are generated by absorption of photons emitted from an energy source such as a laser beam. The absorption and subsequent emission have a lag time of about 10 nsec during which period the molecule exists in an electronically excited state. Because of the short life times of these excited species, fluorescence is widely used to gain kinetic information of interactions and reactions between biomolecules by attaching fluorophores to these molecules. However, when the fluorophore tagged biomolecules are attached to a support system, such as a membrane, it is imperative that the

TABLE 4

| Membrane | Thickness Dry ($\mu$m) | Thickness Wet ($\mu$m) | Wet Cross Section (cm$^2$) | Elastic Modulus (N) | Elastic Modulus (MN/m$^2$) | Break Load Stress (N) | Break Load Stress (MN/m$^2$) | Strain at Break (%) |
|---|---|---|---|---|---|---|---|---|
| Metricel (0.2 RFPD) | 16.3 | 16.5 | .042 | 253 | 6.0 | 6.4 | 0.15 | 6.1 |
| Metricel 0.2 (Unmod) | 16.4 | 16.8 | .043 | 238 | 5.5 | 7.5 | 0.17 | 18.6 |
| Metricel (0.1 RFPD) | 8.6 | 8.6 | .022 | 214 | 7.7 | 4.5 | 0.21 | 5.5 |
| Metricel 0.1 (Unmod) | 7.9 | 8.4 | .021 | 218 | 10.4 | 7.3 | 0.35 | 37.5 |
| Celgard (0.04 RFPD) | 2.8 | 2.8 | .007 | 406 | 580.0 | 9.9 | 14.2 | 12.7 |
| Celgard 0.04 (Unmod) | 2.9 | 2.9 | .007 | 450 | 643.0 | 10.0 | 14.3 | 217.0 |
| Celgard (0.02 RFPD) | 2.8 | 2.9 | .007 | 460 | 657.0 | 10.2 | 14.6 | 6.6 |
| Celgard 0.02 (Unmod) | 2.8 | 2.8 | .007 | 520 | 743.0 | 53.4 | 76.3 | 40.0 |

N = newtons
MN = meganewtons
Metricel (0.2 RFPD)
RFPD = Surface Modified With Ammonia Using Radio Frequency Plasma Discharge
Unmod = Unmodified Membrane Of the above, the unmodified Celgard membranes, which are made by the stretching method and have lamellar and fibrillar microstructures, are slightly stronger than the phase-inversion produced unmodified Metricel membranes which have lacelike microstructures. When loaded perpendicular to its lamellar direction, the Celgard membranes show high elongation at a constant load before break. When loaded parallel to the laminar membrane not exhibit background fluorescence to a degree that it will interfere with the detection and reading of the fluorescence of the biomolecules.

To show comparative background fluorescence of various electroblotting membranes, including the modified polypropylene membranes illustrated above, a preliminary comparison of the fluorescence emission spectra of these materials was made. The fluorescence displayed by these membranes was measured. The membranes were fixed on a coordinate board movable along both the x and y axis by a controller (Daedal. MC 3000). A 50 mW 488 nm monochromatic laser beam was incident at an angle of 45 degrees. The laser was generated by an Argon Ion Laser (Cooper Laser Sonics, Lexel Model 96) with a power supply (Lexel Model 95). The fluorescence was collected by a 50mm Pentax camera lens, focused, filtered and then grated by a Spex Model 1681 spectrometer and detected by a Charge Coupled Device (CCD) camera (Photometric, Ch210). The spectra were output to a personal computer which also controlled the detection process. All of the membranes used have distinct microstructures and void percentages, both affecting light scattering and the effective number of fluorescent molecules. Therefore, the fluorescence backgrounds measured are not exactly the intrinsic properties of the original polymers but are those of the membranes in the form in which they are used.

Although fluorescence spectra from wavelengths ranging from 480 to 600 nm were collected, the fluorescence intensity at 510 nm is shown in Table 5 and is representative of the data across the entire range.

TABLE 5

| Polymer | Fluorescence Intensity | |
|---|---|---|
| | Pixel No. | Relative |
| Nylon 66; (GeneScreen 0.45 μm, DuPont) | 4500 | 60.0 |
| Nitrocellulose; (Nytran, Schleicher and Schull) | 3500 | 46.7 |
| Nylon, quaternary amine surface modified; (Zeta Probe 0.45 μm, Bio-Rad) | 400 | 5.3 |
| Nitrocellulose; (Biotrace NT 0.45 μm, Gelman) | 4000 | 53.3 |
| Polyvinylidene difluoride (PVDF); (Immobilon 0.45 μm, Millipore) | 2650 | 35.3 |
| Polypropylene; (Metricel 0.2 μm; Gelman) (Surface modified by ammonia using RFPD) | 250 | 3.3 |
| Polypropylene; (Metricel 0.1 μm; Gelman) (Surface modified by ammonia using RFPD) | 175 | 2.3 |
| Polypropylene; (Celgard 0.04 μm; Celanese) (Surface modified by ammonia using RFPD) | 300 | 4.0 |
| Polypropylene; (Celgard 0.02 μm; Celanese) (Surface modified by ammonia using RFPD) | 200 | 2.7 |
| Polytetrafluoroethylene (PTFE); (Fluoropore 0.5 μm, Millipore) | 75 | 1.0 |

The nylon (GeneScreen) membrane has a very high fluorescence background as noted by its relative intensity of 60 as compared to 1 for PTFE. The PVDF (Immobilon) and nitrocellulose (Nytran and Biotrace) membranes also had unacceptably high backgrounds. The quaternary amine derivatized nylon (Zeta-Probe) possesses acceptably low fluorescence but shows very low efficiency in actual hybridization experiments with DNA. The PTFE membrane (Fluoropore) exhibits the lowest background fluorescence but unfortunately shows low DNA binding. However, upon appropriate surface modification with amino groups as demonstrated by acceptable DNA binding, PTFE membranes might actually be preferred. At present, surface modified polypropylene membranes possess the best DNA binding capabilities and also exhibit low background fluorescence. For that reason they are presently preferred.

DNA Binding to NH₂ Derivatized Membranes

The chemical binding capability of DNA segments transferred from electrophoretic sequencing gels onto NH₂ derivatized membranes as described above, can be characterized by the binding of $^{32}$P-labeled DNA segments and subsequent liquid scintillation counting of the radioactivity present on the surface modified membranes. When homogeneously mixed in a polyacrylamide electrophoresis gel, the $^{32}$P-labeled DNA is transferred from the gel onto the membranes by an applied electric field using a standard electroblotting process such as Polyacrylamide Gel Electrophoresis (PAGE). For reference purposes a typical PAGE procedure is disclosed by Maniatis et al, Molecular Cloning A Laboratory Manual, Cold Spring Harbor Laboratory, 1982.

The amino groups on the polypropylene (PP) membrane surface are positively charged in the electroblotting buffer at neutral pH as shown in the following formula:

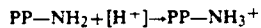

PP—NH$_2$ + [H$^+$] → PP—NH$_3^+$

The polyanionic DNA segments can be physically adsorbed on the polymer membrane surface by at least two mechanisms, i.e. (1) through coulombic interaction with the positively charged amino groups, and (2) through hydrophobic interactions between the nucleotide bases and the polymer substrate. The amount of radioisotope labeled DNA which is physically adsorbed on the polymer surface is proportional to the membrane bound radioactivity and can be measured via a liquid scintillation counter after washing the membranes with electroblotting buffer to remove loosely bound DNA.

The DNA segments physically adsorbed to the membrane surface can be chemically linked to the surface by reaction with crosslinking agents such as glutaraldehyde, bisoxiranes (e.g. 1,4-butanediol diglycidylether), divinylsulfone, dimethylsuberimidate and similar non-aromatic bifunctional reagents with affinity for amino-groups. Crosslinking may also be accomplished by means of ultra-violet radiation. Glutaraldehyde is the preferred crosslinking agent. The chemical linking of the DNA to the surface of an NH₂ modified PP membrane with glutaraldehyde is shown in the following formula:

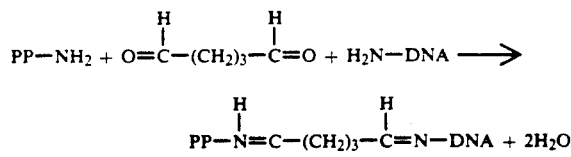

It is preferable to use elevated temperatures of between about 37 and 100 degrees C. for a time period of between about 1 and 5 minutes in the crosslinking reaction Without heat, the reaction may take an hour or more to obtain satisfactory linking. To suppress background fluorescence, it may prove advantageous to reduce the Schiff base complexes to secondary amines by treatment with a reducing agent such as sodium borohydride.

An alternative crosslinking method involved the use of ultraviolet (UV) radiation which is commonly used when attaching DNA sequences to nylon membranes. Because of the aromatic pi-bond in purine and pyrimidine bases, nucleic acids have a strong absorption of UV light near 260 nm. The most effective photoreaction in DNA appears to occur at thymine base. The main photoreaction product found in UV-irradiation is thymine dimer. Two thymines connected by a cyclobutane ring result from the UV cleaved pi-bonds. Although this reaction is reported in the literature [Anal. Chem., 60, No. 6, 381 (1988)], the crosslinking mechanism is still not fully understood. However, this method, although less preferred than treatment with chemical crosslinking agents, is functional for use with membranes surface modified to contain amino groups.

Once the DNA is chemically linked to the membrane, it is preferable to passivate the membrane surfaces to remove any active aldehyde groups and enhance the efficiency and signal to noise ratio in the hybridization probing procedure. A preferred passivating agent is ethanolamine. The passivation reaction is shown as follows:

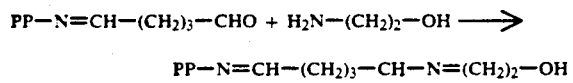

The free aldehyde groups, instead of being reacted with an agent such as ethanolamine, may be reduced to —OH groups by treatment with neutral to alkaline solutions of sodium borohydride. This treatment should further reduce the background fluorescence displayed by the membrane-DNA composite.

The small and mobile ethanolamine easily reaches and reacts with the fixed aldehyde groups. The reaction provides —OH groups on the surface instead of the reactive —CHO groups which cuts down non-specific adsorption by blocking these functional groups and also by the reduction of the hydrophobic interaction.

Following the chemical crosslinking, the membranes are treated in a strong ionic detergent solution such as sodium dodecyl sulphate (SDS) to wash off any non-chemically bound DNA residue. The degree of chemical binding capability can be measured with the liquid scintillation counter.

There follows a description of a procedure used to determine the comparative binding capabilities of various polypropylene and nylon membranes.

The reagents used are as follows. The DNA is a single strand TKZ 52 mer. The radioisotope label is a-$^{32}$P-dAATP, 10 $\mu$Ci/$\mu$l and 370 MBq/ml in Tricine solution (DuPont). The '10×Magnesium reaction buffer solution consists primarily of MgCl$_2$ (Int. Biotechnologies, Inc. Cat. #20125). The enzyme used for the labeling reaction is terminal dideoxynucleotidyl transferase (TdT, Pharmacia), 20 unit/$\mu$l. Reagents used for the gel casting include (1) urea (Sigma, enzyme grade), (2) acrylamide stock solution, which is a 38% acrylamide and 2% bisacrylamide aqueous solution, (2) TBE electrotransfer buffer which contains 10.8 g Tris base, 5.5 g. Boric acid and 0.97 g Na$_2$EDTA in one liter of aqueous solution, (4) 10% ammonium persulphate (APS) in aqueous solution and (5) crosslinking catalyst N,N,N',N'-tetramethylethylenediamine (TEMED, Bio-Rad). The DNA fixation reagent is diluted from a 25% glutaraldehyde aqueous stock solution (Sigma) with ethanol, and the passivation reagent is diluted from 99% pure ethanolamine (Kodak). The ionic detergent SDS is provided in 20% aqueous solution.

Labeling of DNA and Sequencing Gel Preparation

To an Eppendorf tube is added 20 ng TKZ 52 mer, 100 $\mu$uCi a-$^{32}$P-dATP and 10 $\mu$l 10×Mg reaction buffer which is then diluted to a total volume of 100 $\mu$l with distilled water. After adding 1.0 ul TdT enzyme (20 units/$\mu$l), the above mixture is incubated at 37 degrees C. in a water bath for 30 minutes.

A casting set is made by clamping two glass plates together with 0.2 mm PTFE spacers. The side and bottom edges are sealed with tape to prevent leakage of the gel solution to be injected. The glass plates are siliconized by applying very thin films of siliconizing solution (1:19 of dichlorodimethyl silane/chloroform) on the inner glass surfaces. The gel solution is prepared by mixing 17.2 g urea, 6 ml acrylamide stock solution, 4 ml 10×TBE and distilled water to a total volume of 40 ml. The solution is stirred by a magnetic stirrer for 20 minutes followed by vacuum filtration with a Nalgene disposable filter to remove any undissolved particles.

To form a homogeneously mixed DNA gel, the labeled DNA is added to the filtrate and stirred gently. This step is omitted if a pure gel is needed. To effect polymerization, there is added 0.4 ml of a 10% APS solution followed by 30 $\mu$l TEMED catalyst and the mixture is whirled gently. The solution is injected into the space between the two glass plates via a 50 ml syringe. The top edge of the gel is then covered with a plastic film (Saran Wrap) to retain humidity and the gel is kept horizontally until set (about 30 minutes).

Electroblotting

After the gel is set, one glass plate is taken off leaving the gel on the other plate. A Whatman filter paper is put on the exposed gel surface and the other plate is removed exposing the opposite surface. The gel is flushed with 0.5×TBE and the exposed surface is covered by the electroblotting membrane with care being taken to prevent any trapped air between the membrane and gel. The gel and membrane are clamped between two pieces of scotch-brite pads and two plastic grids to retain good contact between the gel and electroblotting membrane. This sandwich is then inserted into an electroblotting chamber filled with 0.5×TBE with the gel being on the cathode side of the membrane. A DC current is applied and run at 1 amp for 30 minutes to transfer the polyanionic DNA segments from the gel onto the membrane surface. The sandwich is removed from the chamber and the membrane is separated from the gel.

Crosslinking

The electroblotting membrane containing the physically adsorbed DNA is washed with electroblotting buffer to remove loosely bound DNA and counted using a liquid scintillation counter in the manner described below to determine the physical adsorption capabilities of the membrane. The membrane is then sprayed evenly with a 5% glutaraldehyde in ethanol solution, covered with a plastic film and baked in an oven (or under a heating lamp) for 1 to 5 minutes between a temperature of 37 and 100 degrees C. to effect the chemical crosslinking between the amino groups of the surface of the membrane and the glutaraldenyde. After heating, unreacted aldehyde moieties on the membrane are passivated by treatment with ethanolamine at different concentrations for various lengths of time. Optimal conditions are thought to be treatment for about 3 minutes with 0.01N ethanolamine. The membrane is then washed with a 5% SDS solution to remove loosely bound DNA segments and other undesired chemicals. The membrane is then ready for scintillation counting to determine its chemical binding capacity for DNA.

An alternative, but less preferable procedure, is to crosslink the DNA segments to the membrane using UV irradiation. A suitable procedure is to subject the membrane to a UV lamp at 0.6 mW/cm² for 4 minutes followed by a 10 minute baking at 100 degrees C.

Scintillation Counting

The counting of the $^{32}$P labeled DNA fragments was done using a microprocessor-controlled spectrometer (Beckman 3801) and counting radioactive decay. The samples were measured by Cerenkov radiation which is operated in aqueous solution instead of scintillation liquid. The exchange from the charged particle, emitted from the radiation source, to the water creates a polarization along its path. When the excited water molecules return to their ground state, the excess energy is released as photons which are then detected by a photomultiplier tube which converts their frequency into an electric signal. A multichannel analyzer accumulates the number of pulse (counts) in each channel. The data can be used to determine the particle energy and the rate of radioactive decay, which is represented in 'counts per minute' (CPM). One microCurie is equivalent to 0.95 million CPM. A major advantage of Cerenkov counting is that the sample can be recovered unchanged and used for further experiments which would not be possible in scintillation fluid counting. In this work, sequential treatments were measured on the same sample using Cerenkov counting.

The Cerenkov counting, in CPM, is recorded in Table 6 showing results of both physical and chemical binding on surface modified polypropylene membranes (Metricel and Celgard), on unmodified polypropylene (Metricel) and on nylon.

TABLE 6

| Polymer | Counts Per Minute | |
|---|---|---|
| | Physical Adsorption | Chemical Binding |
| Polypropylene; (Metricel 0.2 μm; Gelman) (Surface modified by ammonia using RFPD) | 16,800 | 14,400 |
| Polypropylene; (Metricel 0.1 μm; Gelman) (Surface modified by ammonia using RFPD) | 14,900 | 13,900 |
| Polypropylene; (Celgard 0.04 μm; Celanese) (Surface modified by ammonia using RFPD) | 10,000 | 9,000 |
| Polypropylene; (Metricel 0.2 μm; Gelman) (Surface unmodified) | 11,700 | 300 |
| Nylon 66; (GeneScreen 0.45 μm, DuPont) | 5,900 | 5,300 |

The above data clearly demonstrates that the polypropylene membranes, surface modified by RFPD treatment with ammonia, show both higher physical DNA adsorption and chemical DNA crosslinking than does the nylon membrane which is now commercially used for DNA multiplexing sequencing. The unmodified polypropylene membrane, although physically retaining a significant amount of DNA after electroblotting, chemically binds virtually no DNA fragments.

While the chemical binding capability of the membranes is substantially proportional to the degree of amino group introduction, care should be taken to make sure that overbinding of DNA does not occur. In a DNA identification process, the membrane attached DNA fragments will be probed and recognized by the appropriate fluorescence or radioisotope labeled complementary strands. It is very important that the attachment process does not prohibit this pairing. A highly efficient binding process, although desirable from a stability point of view, may force the membrane bound DNA strands into a conformation which is unrecognized by the probe and thereby impair detection. In the glutaraldehyde treatment, in which the bifunctional aldehyde reacts to bridge amino groups on the membrane and amino groups on the DNA bases, free amino groups on the membrane surface may react with the glutaraldehyde leaving a free or reactive aldehyde group. These free aldehyde groups can potentially form covalent linkages with the probes, giving an undesirably high background of fluorescence or radioactivity. Also, over a period of time, they can bind to target DNA chains and increase the number of attachment points thereby decreasing the hybridization probing ability. The passivation of these —CHO groups with an agent, such as ethanolamine, is therefore an important function of preparing the DNA bound membranes for reading. The hybridization activity decreases as the density of binding positions of the DNA segments increases. Therefore, the hybridization efficiency is considered proportional to the degree of passivation. Stated differently, once the DNA strands are chemically bound to the membrane, the introduction of ethanolamine creates a competition mechanism between the ethanolamine and bound DNA for additional binding sites thereby reducing overbonding of the target DNA.

It is evident from the above that the binding capacity of the polypropylene membranes derivatized by the addition of amino groups to the surface are clearly superior to underivatized polypropylene membranes and also to nylon membranes in terms of both physical and chemical binding capacities.

It will now be shown how such membranes can be utilized in the sequencing of DNA fragments.

DNA Sequencing and Hybridization

As referred to above, the DNA sequencing method utilized herein is based on Sanger's 'chain terminating' sequencing method. The DNA samples to be sequenced are first denatured and precipitated to obtain single strand templates. Primers are then annealed with the template to initialize the formation of complementary chains during the sequencing reaction. When the template/primer complex is incubated with DNA polymerase (such as Sequenase) in the presence of a mixture of the A,G,C,T deoxynucleotides spiked with, for example, dideoxy ATP (ddA), the chain is extended from the 5' to the 3' end, until, by chance, a ddA is incorporated into the polymer which effectively stops any further extension of the chain. Thus, a mixture of fragments of different lengths is obtained, which all have the same 5' end, and all are terminated at a ddA residue. Because ddA contains no 3'-hydroxyl group, the phosphodiester chain cannot grow any further once ddA participates in the reaction. Therefore, the specificity of this protocol is much higher than that of the 'chemical cleavage' or Gilbert method. Similar reactions take place in the other mixtures, i.e. dd/dGTP, dd/dCTP and dd/dTTP, with chains terminated at G, C and T residues, respectively.

These mixtures of copied DNA are then fractionated, according to their chain length, by the Polyacrylamide Gel Electrophoresis (PAGE) procedure previously referred to. Following the separation step in the gel, the pattern of bands of DNA fragments separated is transferred onto a membrane using this electroblotting procedure. The fragments are initially attracted to the electroblotting membrane by physical forces and are subsequently crosslinked by chemical bonding to the membrane by means of a crosslinking agent or UV irradiation. When using a chemical crosslinking agent to attach the DNA fragments to the membrane, the unreacted crosslinking agents, which might otherwise provide undesired binding sites for the probe DNA used during detection, are quenched by a passivating agent such as ethanolamine as previously described or by reduction with, e.g. sodium borohydride. In this invention, the detection of the pattern of bands is based on the hybridization of the membrane-linked target DNA using fluorescent or radioisotope labeled probes which are complementary to a specific region of the target DNA.

Field of Application

For experimental purposes, a single stranded DNA of known sequence can be utilized. When using double helix DNA it must first be denatured to form a single DNA strand which can then be used as a template and annealed to a primer for the formation of copied complementary DNA fragments chain terminated at specific bases as described above. It should be noted that the methods described herein are applicable to the formation of complementary nucleic acids or base pairs which can be either DNA/DNA or DNA/RNA. Therefore, just because the description is directed to DNA sequencing it could also be applicable to the sequencing of RNA fragments also. Because the specificity and sensitivity of the hybridization methods are powerful when applied to the 'multiplex sequencing' of DNA as referred to by Church et al, supra, a mixture of multiple DNA samples, instead of a single sample as in conventional methods, can be enzymatically replicated, gel fractionated and electro-transferred to a membrane as described herein. The determination of a specific region of a cloned DNA, the measurement of a number of copies of a specific gene, and the in situ localization of a specific DNA segment in a chromosome are but examples of processes in which hybridization probing of DNA segments bound to the derivatized membranes as described herein can be utilized.

A significant advantage of the invention is that, once the DNA fragments are membrane-linked, they can be immersed and hybridized with a fluorescent or radioisotope labeled probe to identify the pattern of bands of a given DNA sequence. After detection or identification, the labeled probe is removed by washing the membrane with an ionic detergent solution at a high pH to denature the probe and remove it from the membrane bound DNA. This cycle can then be repeated with subsequent probings as long as the membrane bound DNA can bind adequate amounts of DNA.

There follows a method of preparing a DNA sample for dideoxy chain terminating sequencing reaction.

Reagents and Solutions

The dideoxy sequencing reaction utilizes the following reagents and/or solutions.

Solution I is a mixture of 25 mM Tris borate, 10 mM EDTA, 50 mM Glucose, and 0.2% Lysozyme at pH=8.0.

Denaturation solution is a mixture of 1.0N NaOH and 1 mM EDTA.

10×Annealing buffer is a mixture of 100 mM Tris borate and 50 mM $MgCl_2$ at pH=8.3.

Stop solution is a mixture of 98% formamide, 5 mM EDTA and 0.1% of each of the 'tracking dyes' xylene cyanol (Eastman Kodak) and bromophenol blue (Sigma Chemicals).

Kinase buffer is a mixture of 0.5M Tris borate, 0.1M $MgCl_2$, 50 mM DTT and 1 mM EDTA at pH=7.6.

Termination mixtures contain 80 μM dNTP and 8 μM ddNTP, where N=A, G, C and T.

Ethanol is ultrapure and is stored at −20 degrees C. before use.

DNA Preparation

After dish cloning and liquid culture, 1.5 ml culture solution is spun in an Eppendorf tube and resuspended in 100 ul of Solution I. The mixture is kept on ice for 5-10 minutes followed by addition of 200 μl Denaturation solution together with 150 ul 3.0M sodium acetate (pH=8) and inverted to mix for an additional 5-10 minutes The mixture is then spun for 3 minutes and the supernant is pipetted into a new Eppendorf tube and the pellet is discarded.

After adding 20 μl RNAse, the new tube is incubated in a 37 degree C. water bath for 30 minutes followed by adding an equal volume of $CHCl_3$/phenol (1:1) solution and spun for 3 minutes. To precipitate the DNA, 80 ul of −20 degree C. ethanol is added and the solution is let stand for 5 minutes. After spinning the mixture for 5 minutes, the supernant is discarded and the remainder is speed-vacuum dried to obtain a DNA pellet. The pellet is dissolved in distilled water to a proper concentration for future sequencing use.

Dideoxy Sequencing

The description of this procedure is based on the use of a DNA mixture made up of 10 sequences of KZ series DNA of equal concentration. For 48 lane loading, 50 μg of the DNA mixture (10 sequences of KZ series, 5 μg each) is pipetted into an Eppendorf tube with 10 ul Denaturation Solution to denature at room temperature for 5 minutes To the tube is added 7 μl 2.0M ammonium acetate (pH=4.5) followed immediately by the addition of 140 μl ultra pure ethanol. The mixture is incubated at −20 degrees C. for 20 minutes whereupon the sample is spun down for 5 minutes and rinsed with 1 ml of 70% ethanol followed by vortexing and another 5 minute spin. The supernant is removed and the residual is speed-vacuum dried to obtain a pellet.

To the tube containing the pellet is added 3 μl of 10×Annealing Solution, 5 μl Babel primer solution, 5 μl Universal primer solution and distilled water to a total volume of 30 μl. The mixture is incubated at 37 degrees C. for 20 minutes. An extension buffer is prepared by mixing 3 μl 10×Annealing buffer, 3 ul 0.01M DTT, 3 ul DNA polymerase (Sequenase) and distilled water to a total volume of 30 μl. After cooling down to room temperature, the sample is combined with Extension buffer to a total volume of 60 μl and incubated at room temperature for 2 minutes.

To each of four labeled tubes, which contain 12 μl of Termination mixture of d/ddA, d/ddG, d/ddC and d/ddT respectively, was added 14 μl of the above DNA solution. The tubes were labeled A, G, C and T. The tubes were pre-warmed to 37 degrees C. and incubated in a water bath at that temperature for 5 minutes after which 26 μl of Stop solution was added to each tube. The contents of each tube are now ready to be loaded on the polyacrylamide sequencing gel.

Gel Electrophoresis

A series of 6% polyacrylamide gels is casted between glass plates in the manner described above with the exception that no DNA is mixed into the gel solution. After the gels have set, the tops are rinsed with distilled water and the 'sharktooth' side of sample applicator is inserted into the space between the plates until it just touches the gel. The gel slab is clamped into an electrophoresis kit and the upper and lower chambers are filled with 1×TBE. The glass plates on either side of the gel are covered with metal plates to obtain more uniform heat transfer Before introducing the DNA sample onto the gel, the system is pre-run for 20 minutes with the negative electrode being located on top.

After blowing out any bubbles trapped between the teeth of the sample applicator, 4 μl portions of the four sequenced DNA mixtures are loaded in lanes labeled A, G, C and T respectively and a current of 28 mA is applied. The separation of the DNA fragments is monitored by the movement of the dyes which were contained in the Stop solution. The blue tracking dye (Bromophenol blue) which moves at the front, represents about 30 bases and the slower moving green dye (Xylene cyanol) represents about 100 bases. Thus, the resolution range is indicated by the positions presented by the two tracking dyes.

Electroblotting

After the fractionation of the DNA fragments in the gel, the gel is removed and one glass plate is taken off leaving the gel on the other plate. Using the same procedure for electroblotting described above, a Whatman filter paper is put on the exposed gel surface and the other plate is removed exposing the opposite surface. The gel is flushed with $0.5 \times$ TBE and the exposed surface is covered by the electroblotting membrane with care being taken to prevent any trapped air between the membrane and gel. The gel and membrane are sandwiched between two pieces of scotch-brite pads and two plastic grids to retain good contact between the gel and electroblotting membrane and inserted into an electroblotting chamber filled with $0.5 \times$ TBE with the gel being on the cathode side of the membrane. A DC current is applied and run at 1 amp for 30 minutes to transfer the polyanionic DNA segments from the gel onto the membrane surface. The sandwich is removed from the chamber and the membrane is separated from the gel.

Crosslinking

The electroblotting membrane containing the physically adsorbed DNA is washed with electroblotting buffer to remove loosely bound DNA. The membrane is then sprayed evenly with a 5% glutaraldehyde in ethanol solution, covered with a plastic film and baked in an oven for 3 minutes at a constant temperature of 65 degrees C. to effect the chemical crosslinking between the amino groups of the surface of the membrane and the glutaraldehyde. After heating, unreacted aldehyde moieties on the membrane are passivated, converted to —OH groups, by treatment with 0.01N ethanolamine for three minutes. The membranes are then ready for the hybridization procedure with a labeled probe.

Probe Preparation

Although the use of fluorophore labeled probes is preferred, the data presently available showing how the membranes may be used is through radioisotope labeled probes. To prepare the probes a mixture is made up by adding to an Eppendorf tube 20 μg of DNA (TKZ primer or one of the KZ probe series), 80 μ Ci d-$^{32}$P-dATP, 10 ul $10 \times$ Mg reaction buffer and diluted to a total volume of 100 ul with distilled water. After adding 1 ul TdT enzyme, the mixture is spun for 5 seconds and then incubated at 37 degrees C. for 2 hours. Super hot tailed single strands are obtained having a polyadenosine segment linked to the primer.

Hybridization and Detection

The $^{32}$P labeled probe is denatured in a 100 degree C. steam bath for 2 minutes and mixed with 10 ml hybridization buffer in a sealable plastic food storage bag. The membranes prepared according to the above procedures are pre-equilibrated with hybridization buffer, placed in the plastic bag containing the probe and sealed in such a manner as to trap as few air bubbles as possible. The hybridization is carried out while the bag is shaken and incubated at 42 degrees C overnight.

After hybridization, the membranes are removed from the plastic bags and shaken in 100 ml washing solution at 42 degrees C. for 5 minutes. The washing cycle is repeated five times in order to remove all non-hybridized probe. The membranes are now ready for reading. To obtain the autoradiogram, the membrane is covered with a plastic film (Saran Wrap) and suitably sized x-ray film. In order to obtain sharp bands, the film and membrane are pressed together to keep good contact. After adequate exposure, the film is developed by an automatic film developing machine such as Kodak, X-OMAT M35a.

After the autoradiogram is taken the membrane is prepared for the next probing cycle by being washed three times, for 5 minutes each, with 100 ml stripping solution to disrupt the hydrogen bonds between the probe and target strands. The membranes are then neutralized with 200 ml neutralization solution followed by equilibration in hybridization buffer. They are then ready for reprobing.

When using fluorophores as labeling agents, the fluorophore labeled probe is hybridized with the target DNA in the same manner as is the radioisotope labeled probe. However, the sequence ladders are identified by laser induced fluorescence. The data can be put into a computer directly from the fluorescence detector without the exposure to an x-ray film and manual reading as required by radioactive probes. The detection and data readout of the tagged DNA bound to the derivatized membranes is accomplished by state of the art equipment and techniques. The process utilized above in detecting the fluorescence background of the derivatized membranes is applicable to the detection and reading of tagged DNA bound to the membranes. The fluorescent species are those with low non-radiative relaxation. Substances exhibiting significant fluorescence usually possess delocalized electrons present in conjugated double bonds with a rigid molecular skeleton. The loss of vibrational and rotational freedom in the dye molecule causes a larger energy gap between the ground state and the first excited state, which, in turn, leads to strong fluorescence. Typical examples include fluorescein, rhodamine, coumarin and pyrene and their derivatives.

Hybridization Probing Efficiency

The invention does not lie in the discovery of multiplex DNA sequencing or in the broad concept of binding a DNA molecule to a solid support, such as a nylon or nitrocellulose membrane. Nor does the invention reside in the discovery of hybridization probing and detection. Rather, the invention resides in the discovery of and use of a surface modified membrane providing both superior DNA binding capabilities and low background fluorescence. This greatly speeds up the probing and detection process and allows the use of tagging of DNA segments with either fluorophores, which can then be scanned and detected by state of the art laser induced fluorescence, or radioisotopes. Moreover, the probing cycle can be repeated many times with different probes before removal of the target DNA from the membrane. The membrane can then be reused by having fresh DNA samples electroblotted onto and secured to its surface.

The following shows the efficiency of the aminated Metricel 0.2 polypropylene membranes as compared to unmodified Metricel 0.2 polypropylene and the commercially used Genescreen nylon membranes. For comparative purposes relative to a showing of non-specific probe binding, some membranes did not have target DNA electroblotted onto their surfaces. However, each membrane was subjected to a crosslinking treatment with either UV light or glutaraldenyde prior to hybridization probing to minimize non-specific binding sites. To those membranes subjected to electroblotting, the target DNA (TKZ 52 mer) was homogeneously mixed in a polyacrylamide gel and electroblotted onto the selected membranes in the manner already described above. Each membrane had an identical surface area of 1.6 cm$^2$. The probe used was a $^{32}$P-labeled TKZ 32 mer, used as the primer of TKZ. Prior to hybridization probing, each membrane was treated with either UV or 5% glutaraldehyde in ethanol solution followed by passivation with 0.01N ethanolamine. After overnight probing of the membranes following the procedure described above, each membrane was washed five times and the radioactivity on each membrane was determined by Cerenkov counting in the manner also described above. Following the counting each membrane was washed with stripping solution to denature the probes from the target DNA and wash them from the membrane as described above. The membranes were then neutralized with neutralization solution and again read by Cerenkov counting to determine the degree of removal of the labeled probes. Each membrane was then equilibrated with hybridization buffer and the probing cycle repeated. The results obtained are shown in Table 7:

TABLE 7

| Membrane | Cross-Linking | Electro-Blotting | Counts per Minute | | |
|---|---|---|---|---|---|
| | | | 1st Probe | Stripped | 2nd Probe |
| Nylon | UV | Yes | 540 | 105 | 480 |
| Nylon | UV | No | 260 | 95 | 360 |
| PP (RFPD) | UV | Yes | 700 | 105 | 860 |
| PP (unmod) | UV | Yes | 235 | 65 | 170 |
| PP (RFPD) | UV | No | 190 | 85 | 130 |
| PP (RFPD) | GA | Yes | 1,220 | 280 | 1,010 |
| PP (unmod) | GA | Yes | 215 | 85 | 160 |
| PP (RFPD) | GA | No | 365 | 170 | 260 |

Nylon = Genescreen 0.45 nylon membrane
PP (RFPD) = Metricel 0.2 PP membrane surface aminated with RFPD
PP (unmod) = Metricel 0.2 PP membrane unmodified
UV = ultraviolet radiation crosslinking
GA = glutaraldehyde crosslinking and ethanolamine passivation From the above it is apparent that the probe bound to the DNA is much greater in the RFPD surface modified PP membrane than to the nylon membrane. Glutaraldehyde crosslinking of the target DNA to the aminated PP showed increased binding as compared to UV crosslinking. However, both glutaraldehyde and UV crosslinking of the DNA to the aminated PP membranes, show results which are superior to the DNA binding on the nylon membrane. Moreover, the subjecting of the nylon membrane, which had no DNA electroblotted thereon, shows considerable non-specific DNA binding as compared to the aminated PP, also subjected to UV crosslinking, onto which no DNA had been electroblotted. Table 7 also shows that the PP membranes which have either not been aminated by RFPD modification or, if aminated, not had target DNA electroblotted thereon, exhibit very low signals. This indicates that the amination of the membranes is effective and that nonspecific binding with these membranes is negligible. In addition, Table 7 demonstrates that the probe can be effectively stripped from the membranes in preparation for reprobing. Further, the signals from the second probing are comparable to those obtained in the first. Some PP(RFPD) membranes have been reprobed up to 10 times and continue to demonstrate favorable DNA binding specificity and signal to noise ratio which is indicative that the aminated membranes can be expected to continue for a significantly large number of probings. The high signal to noise ratio, or high DNA fluorescence to low fluorescent background, is extremely important to an automated procedure based on fluorescence based detection, particularly when the available amount of DNA to be sequenced is small.

While the above description illustrates the invention in its various embodiments, the invention is not to be limited to the specific embodiments disclosed. Rather, the scope of the invention is limited only by the appended claims and their functional equivalents

We claim:

1. A method for the multiplex sequencing of DNA comprising:
    (a) providing a target DNA sample to be sequenced wherein the DNA fragments have been chain terminated and separated according to a specific adenine, guanine, cytosine or thymine base groupings;
    (b) subjecting base separated groupings of target DNA fragments to gel electrophoresis to resolve the DNA fragments in each base grouping by chain length;
    (c) electroblotting said resolved target DNA fragments from said gel onto the surface of a non-aromatic polymeric microporous membrane said membrane being selected from the group consisting of hydrocarbons, fluorocarbons, chlorofluorocarbons, vinyl alcohols and vinyl chlorides and copolymers and blends thereof and exhibiting low background fluorescence said membrane having been surface modified by subjecting said membrane to an aminating agent in the presence of radio frequency plasma discharge or microwave frequency plasma discharge to contain amino groups in order to physically adsorb said DNA fragments on said membrane surface and washing said membrane to remove unadsorbed DNA fragments;
    (d) treating said membrane containing said physically adsorbed DNA fragments with crosslinking means to chemically bind said DNA fragments to said membrane through said amino groups contained on the surface thereof;
    (e) subjecting said chemically bound DNA fragments on said membrane to hybridization probing with a tagged probe specific to the sequence of the DNA fragments and washing said membranes to remove probe which has not been hybridized; and
    (f) detecting and reading said tagged probes hybridized to said target DNA fragments.

2. A method according to claim 1 wherein said probes are tagged with radiosotopes or fluorophores.

3. A method according to claim 2 wherein said surface modified membrane is a member selected from the group consisting of polypropylene, polyethylene, polytetrafluoroethylene, polyvinylidenefluoride, polyvinylchloride, polyfluoroethylene-propylene, ethylenevinylalcohol, and polyethylene-chlorotrifluoroethylene and blends and copolymers thereof.

4. A method according to claim 3 wherein said aminating group is a member selected from the group consisting of ammonia gas and $C_1$-$C_{10}$ aliphatic or cyclic amines and mixtures thereof.

5. A method according to claim 4 wherein said aminating group is a member selected from the group consisting of ammonia gas, methyl amine, allyl amine, ethylenediamine and diaminocyclohexane and mixtures thereof.

6. A method according to claim 5 wherein the aminating agent is ammonia gas.

7. A method according to claim 6 wherein the membrane has been aminated using radio frequency plasma discharge in the presence of ammonia gas.

8. A method according to claim 7 wherein the membrane is a member selected from the group consisting of polypropylene, polyethylene and polytetrafluoroethylene.

9. A method according to claim 8 wherein the membrane is polypropylene.

10. A method according to claim 9 wherein said crosslinking means comprises irradiating the membrane with ultraviolet light or subjecting the membrane to a chemical cross linking agent.

11. A method according to claim 10 wherein said membrane is subjected to a non-aromatic bifunctional chemical crosslinking agent having an affinity for amino-groups on said DNA fragments and on said membrane to chemically crosslink said DNA to said membrane.

12. A method according to claim 11 wherein said chemical crosslinking agent is a member selected from the group consisting of glutaraldehyde, bisoxiranes, divinylsulfone and dimethylsuberimidate.

13. A method according to claim 12 wherein said chemical crosslinking agent is glutaraldehyde.

14. A method according to claim 13 wherein said membrane is subjected to treatment with ethanolamine to passivate any aldehyde groups which have not reacted with an amine.

15. A method according to claim 14 wherein said probe has been tagged with a fluorophore and is read by means of fluorescent detection.

16. A method according to claim 15 wherein, after said reading, said fluorophore tagged probe is removed from said target DNA fragments bound to said membrane by stripping and said target DNA fragments are reprobed with additional fluorophore tagged probe.

17. A method according to claim 14 wherein said probe has been tagged with a radioisotope and is read by means of an autoradiogram.

18. A method of aminating the surface of a non-aromatic polymeric microporous membrane exhibiting low background fluoroescence, wherein said membrane is selected from the group consisting of hydrocarbons, fluorocarbons, chlorofluorocarbons, vinyl alcohols and vinyl chlorides and copolymers and blends thereof, which comprises subjecting said membrane to an aminating agent in the presence of radio frequency plasma discharge or microwave frequency plasma discharge.

19. A method according to claim 18 wherein said membrane is a member selected from the group consisting of polypropylene, polyethylene, polytetrafluoroethylene, polyvinylidenefluoride, polyvinylchloride, polyfluoroethylene-propylene, ethylenevinylalcohol, and polyethylene-chlorotrifluoroethylene and blends and copolymers thereof.

20. A method according to claim 19 wherein said amination of said surface is accomplished by subjecting said membrane to an aminating agent selected from the group consisting of ammonia gas and $C_1$-$C_{10}$ aliphatic or cyclic amines and mixtures thereof.

21. A method according to claim 20 wherein said aminating agent is a member selected from the group consisting of ammonia gas, methyl amine, allyl amine, ethylenediamine and diaminocyclohexane and mixtures thereof.

22. A method according to claim 21 wherein the aminating agent is ammonia gas.

23. A method according to claim 22 wherein the membrane has been aminated using radio frequency plasma discharge in the presence of ammonia gas.

24. A method according to claim 23 wherein the membrane is a member selected from the group consisting of polypropylene, polyethylene and polytetrafluoroethylene.

25. A method according to claim 24 wherein the membrane is polypropylene.

26. An aminated polypropylene membrane according to claim 25.

* * * * *